(12) United States Patent
Namburi et al.

(10) Patent No.: US 8,071,133 B2
(45) Date of Patent: *Dec. 6, 2011

(54) ORAL DOSAGE FORMS OF WATER INSOLUBLE DRUGS AND METHODS OF MAKING THE SAME

(75) Inventors: Ranga R. Namburi, Greenville, NC (US); Allen L. Lawson, Greenville, NC (US); John E. Kerr, Winterville, NC (US)

(73) Assignee: Stiefel Laboratories, Inc., Coral Gables, FL (US)

( * ) Notice: Subject to any disclaimer, the term of this patent is extended or adjusted under 35 U.S.C. 154(b) by 1734 days.

This patent is subject to a terminal disclaimer.

(21) Appl. No.: 10/617,350

(22) Filed: Jul. 11, 2003

(65) Prior Publication Data

US 2004/0052847 A1  Mar. 18, 2004

Related U.S. Application Data

(63) Continuation-in-part of application No. 09/933,032, filed on Aug. 20, 2001, now Pat. No. 6,663,897.

(60) Provisional application No. 60/401,121, filed on Aug. 5, 2002.

(51) Int. Cl.
*A61K 9/50* (2006.01)

(52) U.S. Cl. ........................................ 424/490

(58) Field of Classification Search ............ None
See application file for complete search history.

(56) References Cited

U.S. PATENT DOCUMENTS

| | | |
|---|---|---|
| 4,149,346 A | 4/1979 | Belt |
| 4,159,345 A | 6/1979 | Takeo et al. |
| 4,160,014 A | 7/1979 | Gamo et al. |
| 4,171,667 A | 10/1979 | Miller et al. |
| 4,196,219 A | 4/1980 | Shaw et al. |
| 4,199,368 A | 4/1980 | McGinley |
| 4,231,802 A | 11/1980 | McGinley et al. |
| 4,234,316 A | 11/1980 | Hevey |
| 4,275,196 A | 6/1981 | Shainoff |
| 4,290,911 A | 9/1981 | Cook et al. |
| 4,319,975 A | 3/1982 | Cook |
| 4,330,338 A | 5/1982 | Banker |
| 4,381,082 A | 4/1983 | Elliott et al. |
| 4,387,164 A | 6/1983 | Hevey et al. |
| 4,415,428 A | 11/1983 | Nochumson et al. |
| 4,462,839 A | 7/1984 | McGinley et al. |
| 4,484,141 A | 11/1984 | Cook et al. |
| 4,504,641 A | 3/1985 | Nochumson |
| 4,518,433 A | 5/1985 | McGinley et al. |
| 4,542,200 A | 9/1985 | Nochumson et al. |
| 4,588,555 A | 5/1986 | Provonchee |
| 4,659,672 A | 4/1987 | Provonchee et al. |
| 4,689,302 A | 8/1987 | Goldberg et al. |
| 4,693,896 A | 9/1987 | Wheatley et al. |
| 4,695,548 A | 9/1987 | Cantor et al. |
| 4,701,754 A | 10/1987 | Provonchee |
| 4,749,620 A | 6/1988 | Rha et al. |
| 4,755,987 A | 7/1988 | Lee et al. |
| 4,774,093 A | 9/1988 | Provonchee et al. |
| 4,861,448 A | 8/1989 | Cantor et al. |
| 4,966,713 A | 10/1990 | Keys et al. |
| 4,983,268 A | 1/1991 | Kirkpatrick et al. |
| 4,990,611 A | 2/1991 | Provonchee |
| 5,051,261 A | 9/1991 | McGinity et al. |
| 5,053,332 A | 10/1991 | Cook et al. |
| 5,075,115 A | 12/1991 | Brine |
| 5,143,646 A | 9/1992 | Nochumson et al. |
| 5,155,144 A | 10/1992 | Manganaro et al. |
| 5,206,030 A | 4/1993 | Wheatley et al. |
| 5,212,299 A | 5/1993 | Smith |
| 5,258,436 A | 11/1993 | Wheatley et al. |
| 5,277,915 A | 1/1994 | Provonchee et al. |
| 5,326,752 A | 7/1994 | Nashed et al. |
| 6,039,981 A | 3/2000 | Woo et al. |
| 6,245,351 B1 * | 6/2001 | Nara et al. ............... 424/461 |
| 6,497,905 B1 * | 12/2002 | Vladyka et al. ............ 424/502 |
| 2003/0012815 A1 * | 1/2003 | Ishibashi et al. ............ 424/471 |
| 2003/0211168 A1 * | 11/2003 | Lynenskjold et al. ........ 424/494 |

FOREIGN PATENT DOCUMENTS

| | | |
|---|---|---|
| EP | 1350508 | 10/2003 |
| WO | WO 94/05263 | 3/1994 |
| WO | WO 98/42318 | 10/1998 |
| WO | WO 00/03697 | 1/2000 |
| WO | WO 00/36697 | 1/2000 |
| WO | WO 02/062318 | 8/2002 |

OTHER PUBLICATIONS

Martindale: The Complete Drug Reference, Pharmaceutical Press, London, 2002, pp. 1344-1349.*

Mathir et al., In vitro characterization of a controlled-release chlorpheniramine maleate delivery system prepared by the air-suspension technique, *Journal of Microencapsulation*, vol. 14. No. 6:743-751 (1997).

* cited by examiner

*Primary Examiner* — James D Anderson
(74) *Attorney, Agent, or Firm* — The Nath Law Group; Joshua B. Goldberg (57) ABSTRACT

A method of making an oral dosage form of a water insoluble drug such as Saquinavir or Cyclosporine or Paclitaxel is carried out by: (a) providing a single phase working Solution comprising or consisting essentially of an active agent, water, a water-soluble polymer, and a solvent, said solvent selected from the group consisting of alcohol, acetone, and mixtures thereof; and may or may not contain a surfactant and pH of the said working solution may or may not be adjusted (b) providing particles formed from a pharmaceutically acceptable core material; (c) combining, preferably by spraying, said working solution with said particles to produce active agent-coated particles; such drug loaded particles may contain an external coat (d) drying said active agent-coated particles; and (e) forming said dried particles into an oral dosage form. Dried particles produced by the process, oral dosage forms containing such particles, and methods of treatment therewith are also described.

15 Claims, 7 Drawing Sheets

Figure 1: Dissolution of Saquinavir Capsules 200 mg (a) of the invention (triangles) and (b) commercial formulation (squares)

Figure 2: Normalized DSC thermogram for Itraconazole activepharmaceutical ingredient Figure 3: Normalized DSC thermogram from Itraconazole loaded beads Figure 4: Normalized DSC thermogram of commercially available itraconazole loaded beads Figure 5: Normalized DSC thermogram of Saquinavir active pharmaceutical ingredient Figure 6: Normalized DSC thermogram of Saquinavir loaded beads Figure 7: Normalized DSC thermogram of Cyclosporine active pharmaceutical ingredient Figure 8: Normalized DSC thermogram of Cyclosporine loaded beads Figure 9: Normalized thermogram of Paclitaxel Active Pharmaceutical Ingredient Figure 10: Normalized thermogram of Paclitaxel Drug Loaded beads Figure 11 - Itraconazole Plasma Concentration under fed condition (ng/mL)

Figure 12 - Itraconazole Plasma Concentration under fasted condition (ng/mL)

ORAL DOSAGE FORMS OF WATER INSOLUBLE DRUGS AND METHODS OF MAKING THE SAME

RELATED APPLICATIONS

This application claims the benefit of U.S. Provisional Patent Application Ser. No. 60/401,121, filed Aug. 5, 2002, and this application is a continuation-in-part of U.S. patent application Ser. No. 09/933,032, filed Aug. 20, 2001 now U.S. Pat. No. 6,663,897, the disclosures of both of which are incorporated by reference herein in their entirety.

FIELD OF THE INVENTION

The present invention concerns methods of making oral formulations of water insoluble drugs, the oral dosage forms so made, and methods of use thereof.

BACKGROUND OF THE INVENTION

Increasing numbers of newly discovered drugs are insoluble (e.g., have a solubility of less than 100 µg per mL as per the definition of United States Pharmacopeia). For example, pharmaceutical compounds such as itraconazole, saquinavir, cyclosporine, paclitaxel, etoposide, etc. have an extremely low solubility in water. Indeed, the solubility of itraconazole in water and 0.1 N hydrochloric acid is less than 1 microgram and 6 micrograms per milliliter, respectively. Saquinavir, an antiviral compound, has approximately 10 microgram per mL solubility in water.

PCT Application WO 94/05263 to Gillis et al. (assigned to Janssen Pharmaceutica) describes 25-30 mesh beads having a core coated with itraconazole or saperconazole, which beads may be used to produce dosage forms of these drugs. To prepare the beads, the drug coating solution is dissolved into a suitable solvent system which is then combined with the beads. However, the only solvent system described is one comprising methylene chloride (dichloromethane) and an alcohol (see page 4, line 4 therein). Methylene chloride is undesirable as a solvent in pharmaceutical systems due to potential toxicological concerns.

PCT Application WO 00/03697 to Gillis et al. (assigned to Janssen Pharmaceutica) describes usage of sugar pellets of 710-1180 µm (25-16 mesh), a coating film of a water-soluble polymer and an antifungal agent, and a seal coating layer wherein the residual concentration of dichloromethane is reduced by microwave drying (page 10, lines 31 to 38).

PCT Application WO 98/42318 to Vandecruys et al., (assigned to Janssen Pharmaceutica) describes 30-60 mesh beads having a core coated with itraconazole or saperconazole, which beads may likewise be used to produce dosage forms of these drugs. To prepare the beads the drug coating solution is, again, dissolved into a suitable solvent system. Again the only solvent system described is one comprising methylene chloride and an alcohol, and it is stated that the methylene chloride should comprise at least 50% by weight of the solvent system (see page 8, lines 32-34 therein).

U.S. application Pat. No. 6,039,981 teaches an antifungal composition for oral administration comprising a fused mixture of itraconazole and phosphoric acid, a pharmaceutically acceptable carrier and a surfactant. Heating of the mixture is done at 100 to 170° C. to obtain a homogeneous mixture (Column 3, lines 16-18). Although example 8 provides a composition that needs to be loaded on to sugar spheres, no dissolution data or stability information in terms of acid and sugar spheres interaction (caramelization) was discussed. The example 8 composition also does not produce a mixture that could be sprayed onto sugar or microcrystalline spheres when the experiment was repeated in our laboratories.

Accordingly, there remains a need for new ways to produce oral dosage forms of water insoluble drugs that utilize coated particles, but do not require the use of methylene chloride or other objectionable solvents during the manufacture thereof. A process that can be industrially applicable, and preferably does not use temperatures above 100° C., that are needed for making fusion mixtures. A process that prevents interaction between core particles and acid or base ingredients or acidity as contributed by Active Pharmaceutical Ingredient itself is needed.

SUMMARY OF THE INVENTION

In one respect, the present invention provides a process of converting crystalline active compounds into an amorphous state during coating or spray coating of core particles. More particularly, this invention relates to a preparation containing an active compound or drug in amorphous state, which allows water insoluble drugs (including poorly water soluble drugs) to have a more rapid speed of dissolution and greater uptake efficiency in the gastro-intestinal tract, and which preparation is convenient to produce as a pharmaceutical formulation.

More particularly, a first aspect of the present invention is a method of manufacturing an active agent oral dosage form. The method comprises the steps of:
  (a) providing a single phase working solution comprising or consisting essentially of an active agent (which may be in the form of a salt, which salt may be formed in situ), water, a water-soluble polymer, and a solvent, said solvent preferably selected from the group consisting of alcohol, acetone, and mixtures thereof,
  (b) providing particles formed from a pharmaceutically acceptable core material;
  (c) combining said working solution with said particles to produce active agent-coated particles;
  (d) drying said active agent-coated particles; and
  (e) forming said dried particles into an oral dosage form.

Optionally, an external coat may be applied to the active agent coated particles, typically after the drying step. The external coating may be of any suitable material, such as polyethylene glycol. A single phase working solution may contain a surfactant to help dissolve the active agent through formation of small particles or vesicles such as micelles or the like.

The active agent oral dosage form and the single phase working solution used in the process of making such dosage form are preferably substantially free of residual methylene chloride (e.g., contains less than 200 ppm methylene chloride, less than 100 ppm methylene chloride, less than 50 ppm methylene chloride, less than 20 ppm methylene chloride, or even less than 10 ppm methylene chloride), and is preferably substantially free of carbon tetrachloride (e.g., contains less than 200, 100, 50, 20, or even 10 ppm, as above for methylene chloride), which solvents have sometimes been employed in older less desirable prior art processes.

In one embodiment of the foregoing, the dried active agent-coated particles preferably comprise, by weight, the active agent in an amount having a lower limit of 1, preferably 5 percent and an upper limit of 50, preferably 40 percent; the particle core material in an amount having a lower limit of 5, preferably 10 percent and an upper limit of 60, preferably 50 percent; and the water-soluble polymer in an amount having a lower limit of 1, preferably 5 percent and an upper limit of 90, preferably 80 percent.

A second aspect of the present invention is a pharmaceutically acceptable particle comprising (a) a central core (e.g., spherical or irregular in shape) comprised of a core material; and (b) a coating film formed on the core, the coating film comprising a water-soluble polymer and active agent. The particle preferably comprises, by weight, the active agent in an amount having a lower limit of 1, preferably 5 percent and an upper limit of 50, preferably 40 percent; the particle core material in an amount having a lower limit of 5, preferably 10 percent and an upper limit of 60, preferably 50 percent; the water-soluble polymer in amount having a lower limit of 1, preferably 5 percent and an upper limit of 90 preferably 80 percent. Preferably the particle is substantially or essentially free of methylene chloride and carbon tetrachloride as described above (e.g., containing less than 200, less than 100, less than 50, less than 20, or even less than 10 ppm of each, as described above).

A third aspect of the present invention is a pharmaceutically acceptable particle comprising (a) a central core (e.g., spherical or irregular in shape) comprised of a core material; and (b) a coating film formed on the core, the coating film comprising a water-soluble polymer, a surface active agent and active agent. The particle preferably comprises, by weight, the active agent in an amount having a lower limit of 1, preferably 5 percent and an upper limit of 50, preferably 40 percent; the particle core material in an amount having a lower limit of 5, preferably 10 percent and an upper limit of 60, preferably 50 percent; the water-soluble polymer in an amount having a lower limit of 1, preferably 5 percent and an upper limit of 90, preferably 80 percent and the surfactant in an amount having a lower limit of 5, preferably 10 percent and an upper limit of 50, preferably 40 percent. Preferably the particle is substantially or essentially free of methylene chloride and carbon tetrachloride as described above (e.g., containing less than 200, less than 100, less than 50, less than 20, or even less than 10 ppm of each, as described above).

A fourth aspect of the present invention is an active agent oral dosage form (e.g., a capsule or tablet) that is substantially or essentially free of residual methylene chloride or carbon tetrachloride (as described above), the formulation comprising a pharmaceutically effective amount of particles as described above. Typically, such a dosage form contains the active agent in an amount having a lower limit of 5, preferably 10, in particular 50 milligrams and an upper limit of 500, preferably 300, in particular 200 milligrams. In preferred embodiments the oral dosage form comprises particles as described above in a dosage form, which dosage form does not contain or comprise a lipid such as medium chain mono- and diglycerides as is found in "soft gel" capsules (in contrast to the hard forms described herein).

A further aspect of the present invention is a method of treating a subject in need thereof, comprising orally administering to the subject an oral dosage form as described above in a pharmaceutically acceptable amount.

An advantage of the present invention is the stability of the particles and oral dosage forms produced by the processes disclosed herein. When administering therapeutic agents such as protease inhibitors (for example, Saquinavir), proton pump inhibitors (for example, Omeprazole), oligopeptides (for example, Cyclosporine), and others, a highly stable formulation is desirable. The chemical stability of a formulation generally refers to the amount of chemical degradation of a particular agent in the formulation. The chemical stability of a formulation depends upon the amount of chemical degradation of active compound in that preparation. Note that stability analysis of pharmaceutical formulations is done under accelerated conditions (high temperature and humidity) to determine dosage form stability on storage. Commonly, stability analysis of a formulation under accelerated temperature conditions, such as in a 50° C. oven provides a rapid assessment of the stability of the active pharmaceutical ingredient when formulated with the selected composition of the dosage form.

The foregoing and other objects and aspects of the present invention are explained in greater detail in the specification set forth below.

DETAILED DESCRIPTION OF THE PREFERRED EMBODIMENTS

"Insoluble" in water as used herein refers to compounds that have a solubility of less than 100 μg per mL in distilled water at 25° C., consistent with the definition given in the of United States Pharmacopoeia. This includes practically insoluble and/or sparingly soluble compounds. Note also that the BioPharmaceutics Classification System (BCS) provides a framework for classifying drug substances based on their aqueous solubility and intestinal permeability. When combined with the dissolution of the drug product, the BCS takes into account three major factors that govern the rate and extent of drug absorption of solid oral dosage forms: dissolution, solubility, and intestinal permeability. According to the BCS, drug substances are classified as follows:

Class 1: High Solubility—High Permeability
Class 2: Low Solubility—High Permeability
Class 3: High Solubility—Low Permeability
Class 4: Low Solubility—Low Permeability Thus, class 2 and class 4 compounds are particularly preferred as active agents in the present invention. Approximate solubility information of USP and NF articles is specified in the United States Pharmacopeia (USP).

In some embodiments it is contemplated to have enhanced in-vitro dissolution with active agents such Saquinavir, Cyclosporine, Paclitaxel and Itraconazole dosage forms when the active ingredients are converted into amorphous forms through the process used in the invention. In some embodiments the hydrophilic polymer acts as a surfactant for enhancing the solubility of the active ingredients in an amorphous state. Some formulations such as Cyclosporine and Paclitaxel require addition of a cosurfactant in the formulations to obtain the desired in-vitro dissolution. Enhanced in-vitro dissolution of Itraconazole formulation results in enhanced oral absorption and it is shown in-vivo studies performed with Itraconazole formulation on humans.

1. Active Agents.

Active agents used to carry out the present invention are water insoluble (or "lipophilic") compounds, as described above. Examples of such active agents include, but are not limited to:

Protease inhibitors such as Amprenavir, Indinavir, Lopinavir, Nelfinavir, Ritonavir, and Saquinavir;

Statins or HMG-CoA reductase inhibitors such as Atorvastatin calcium, Simvastatin, Pravastatin, Fluvastatin, and Lovastatin;

Oligopeptides such as Cyclosporine and Enlimomab;

Proton pump inhibitors such as Omeprazole, Lansoprazole, Rabeprazole, and Pantoprazole;

Steroidal compounds such as Hydrocortisone, Betamethasone;

Antibiotic compounds such as Phenoxymethyl Penicillin, Cefixime, and Cefuroxime Axetil;

Paclitaxel, Etoposide, Cisapride, Doxorubicin, Cholecalciferol, Nefedipine, Digoxin, Aztreonum, Acyclovir, Griseofulvin, Diclofenac, Miconazole, Terfenadine, Indomethacin, Tamoxifen, Cisapride, Diazepam, Digoxin, Propofol, Posaconazole (an antifungal compound having a close structural relationship to that of Itraconazole), and other insoluble drugs.

In one embodiment, the active compounds which may be used to carry out the present invention specifically excludes sparingly water-soluble antifungal agents such as itraconazole, and other azoles such as saperconazole, ketoconazole, fluconazole, and miconazole.

2. Core Particles.

Core particles used herein may be of any suitable size, typically from about 100 to 1000 micrometers in diameter. Examples include particles with a diameter of about 250 to 600 μm (60-30 mesh), or a diameter of 600 to 700 μm (30-25 mesh). Size of particles can be determined in accordance with known techniques, such as described in the CRC Handbook, $64^{th}$ edition, page F-114 and USP24/NF19, page 1969.

The core particles may be formed of any suitable pharmaceutically acceptable material. Examples of such materials are polymers e.g., plastic resins; inorganic substances, e.g., silica, glass, hydroxyapatite, salts (sodium or potassium chloride, calcium or magnesium carbonate) and the like; organic substances, e.g., activated carbon, acids (citric, fumaric, tartaric, ascorbic and the like acids), and saccharides and derivatives thereof. Particularly suitable materials are saccharides such as sugars, oligosaccharides, polysaccharides and their derivatives, for example, glucose, rhamnose, galactose, lactose, sucrose, mannitol, sorbitol, dextrin, maltodextrin, cellulose, microcrystalline cellulose, sodium carboxymethyl cellulose, starches (maize, rice, potato, wheat, tapioca) and the like saccharides.

Preferred as a core material for carrying out the present invention is microcrystalline cellulose particles or spheres, which can be produced in accordance with known techniques as described in U.S. Pat. Nos. 4,159,345; 4,149,346; 4,160,014; 4,196,219; 4,199,368; 4,231,802; 4,234,316; 4,275,196; 4,290,911; 4,319,975; 4,330,338; 4,381,082; 4,387,164; 4,415,428; 4,462,839; 4,484,141; 4,504,641; 4,518,433; 4,542,200; 4,588,555; 4,659,672; 4,689,302; 4,693,896; 4,695,548; 4,701,754; 4,717,667; 4,744,987; 4,749,620; 4,774,093; 4,861,448; 4,966,713; 4,983,268; 4,990,611; 5,051,261; 5,053,332; 5,075,115; 5,143,646; 5,155,144; 5,206,030; 5,212,299; 5,258,436; 5,277,915; 5,326,572; etc.

Currently preferred microcrystalline cellulose spheres are available as CELPHERE spheres from Asahi Chemical Industry, Tokyo, Japan. Of these, CP-507 grade, 600 micrometer diameter CELPHERE microcrystalline cellulose spheres are currently preferred.

The particles or spheres may optionally be protected with a barrier coating prior to formation of the active-containing film thereon, for example in the case where sugar is the core material and the barrier layer is provided to reduce caramelization, for stability and/or cosmetic purposes.

3. Water Soluble Polymers.

Any suitable water-soluble polymer may be used herein. In one preferred embodiment the polymer has an apparent viscosity of 1 to 100 mPa.s when dissolved in a 2% aqueous solution at 20° C. Examples of suitable water soluble polymers include, but are not limited to, alkylcelluloses such as methylcellulose, hydroxyalkylcelluloses such as hydroxymethylcellulose, hydroxyethylcellulose, hydroxypropylcellulose and hydroxybutylcellulose; hydroxyalkyl alkylcelluloses such as hydroxyethyl methylcellulose and hydroxypropyl methylcellulose; carboxyalkylcelluloses such as carboxymethylcellulose; alkali metal salts of carboxyalkylcelluloses such as sodium carboxymethylcellulose; carboxyalkylalkylcelluloses such as carboxymethylethylcellulose; carboxyalkylcellulose esters; starches; pectins such as sodium carboxymethylamylopectin; chitin derivatives such as chitosan; polysaccharides such as alginic acid, alkali metal and ammonium salts thereof, carrageenans, galactomannans, traganth, agar-agar, gum arabicum, guar gum and xanthan gum; polyacrylic acids and salts thereof; polymethacrylic acids and salts thereof, including methacrylate copolymers polyvinylpyrrolidone, copolymers of polyvinylpyrrolidone with vinyl acetate; polyalkylene oxides such as polyethylene oxide and polypropylene oxide and copolymers of ethylene oxide and propylene oxide; dextrins and maltodextrins etc. Currently preferred is hydroxy propyl methyl cellulose, manufactured by Aqualon, USA, Dow Chemical Industries, USA and also by Shin-Etsu Chemical Company, Japan. Preferably 5 mPa.s or 3 mPa.s viscosity grades are used in the process.

4. Solvents.

Alcohols that may be used in the present invention include, but are not limited to, ethanol, particularly denatured ethanol such as SD3A alcohol. Other suitable alcohols include, but are not limited to, methanol, propanol (e.g., isopropyl alcohol), butanol such as tert-butyl, etc., including mixtures thereof. Currently preferred is SD3A alcohol, available from Van Waters & Rogers, Inc., 3600 Windover Avenue, Greensboro, N.C., USA 27407. Any suitable acetone may be used to carry out the present invention, such as Pharmacopeial or USP grade acetone. Acetone and water may be used individually or combined as a solvent, and when combined may be used in any suitable ratio. In one embodiment, water alone without acetone is employed as the solvent.

5. Drug Loaded Particles Manufacture.

In the present invention, the hydrophobic or water insoluble compounds or drugs are generally converted into an amorphous state through the process of dissolving them in a solvent system, either adjusting the pH of the solvent system or not, and using an appropriate hydrophilic polymer and spray coating that system onto particulates. Optionally, a surfactant could be incorporated into the spray coating solution containing active and hydrophilic polymer. The solid dispersed preparation of the invention can be applied for all water insoluble or hydrophobic drugs.

The working solution/solvent system should be prepared with care to insure, among other things, the desired solubilization of the active agent therein. In general, in the working solution, the weight:weight ratio of active agent to water-soluble polymer may have an lower limit of 1:0.5, preferably 1:0.9, most preferably 1:1 and a upper limit of 1:20, preferably 1:10, more preferably 1:5, most preferably 1:2. In addition, the weight:weight ratio of solvent (including all solvents when multiple solvents are employed) to water in the working solution for instance may have a lower limit of 60:40, preferably 50:50, preferably 95:5 most preferably 99:1 or even 99.9:0.1 or more. The viscosity of the working solution should be such as to avoid agglomeration during the combining or spraying step, and in general has a lower limit of about 10, preferably 25, most preferably 40, in particular 60 milli-Pascals and an upper limit of 400, 700, 1000, or 2000 mPa.s. A viscosity range of 10 to 200 mPa.s is preferred.

In one embodiment that utilizes in situ salt formation of the active agent, the method comprises the steps of: (a) providing a working solution comprising or consisting essentially of a solvent (alcohol and/or acetone), an active agent, a strong or weak acid or base (depending on whether the active agent is acidic or basic), a water-soluble polymer, and water (with, for example, the active agent and the acid or base present in the working solution in a ratio of 1 Mole active agent to an amount of acid or base having a lower limit of 1, preferably 1.2, most preferably 2 Moles and an upper limit of 5 preferably 4, most preferably 3, in particular 2.5 Moles); (b) providing particles formed from a pharmaceutically acceptable core material; (c) combining the working solution with the particles to produce active agent-coated particles; (d) drying the active agent-coated particles; and (e) forming the dried active agent-coated particles into an active agent oral dosage form. The in-situ salt formation of the active compound prevents its crystallization from its acidic or basic aqueous solutions.

In other embodiments, it has unexpectedly been found that sufficient solubility of the active agent (e.g., Saquinavir) can be attained without in situ salt formation, so long as alcohol and/or acetone is included in the working solution. Here it may be desirable to first solubilize the active agent in the alcohol and/or acetone before adding the active agent to the remaining ingredients of the working solution.

With some embodiments, it is desirable to incorporate a surfactant for better wetting of the active, hydrophilic polymer mixture to ensure dissolution of active ingredients, such as Cyclosporine and Paclitaxel compositions.

Note that, in the preparation of the working solution, it is generally desirable to include at least some water in the solution prior to adding the water-soluble polymer, to insure that the water-soluble polymer is indeed solubilized in the working solution.

The acids that may be used in the present invention may be strong as well as weak acids. Strong acids that may be used to carry out the present invention may, in general, be inorganic acids or organic sulphonic acids. Examples of inorganic acids that may be used in the present invention include, but are not limited to, hydrochloric acid, sulfuric acid, phosphoric acid, nitric acid, hydrobromic acid, etc. Examples of organic sulphonic acids that may be used to carry out the present invention include, but are not limited, to methane sulphonic acid, ethane sulphonic acid (including derivatives thereof), benzene sulphonic acid, toluene sulphonic acid, naphthalene sulphonic acid, etc. Weak acids such as citric acid, tartaric acid, can also be used to form salts of drugs containing strong basic functional groups.

The bases that may be used in the present invention may be strong as well as weak bases. Strong or weak bases used to carry out the present invention may, in general, be inorganic or organic bases. Examples of inorganic bases that may be used in the present invention include, but are not limited to, alkaline earth metal hydroxides such as sodium hydroxide, potassium hydroxide, ammonium hydroxide, etc. Examples of organic bases include alkanolamines such as monoethanolamine, diethanolamine, triethanolamine, alkylamines such as diethylamine, triethylamine etc.

The particles of the invention are for instance prepared by dissolving the active agent into a solvent system of aqueous alcohol and/or acetone with varying proportions of alcohol and/or acetone and water and, if desired using an acid or base to convert the active compound into a salt form and a water-soluble polymer. The drug coating process, coating of core particles with the working solution containing Active, hydrophilic polymer and or surfactant with or without adjustment of pH, may be conducted in a fluidized bed coater in accordance with known techniques. The spray rate in the coater should be regulated carefully to avoid spray drying of the drug coating solution, or over wetting with subsequent twin formation/agglomeration.

The coating film or layer of the particles described herein may further comprise one or more pharmaceutically acceptable excipients such as, for example, plasticizers, flavors, pigments (e.g., titanium dioxide), preservatives and the like.

In addition, the particles according to the present invention may further contain one or more additional additives such as thickening agents, lubricants, preservatives, complexing and chelating agents, electrolytes or other active ingredients, e.g., antiinflammatory agents, antibacterials, disinfectants or vitamins.

An additional surfactant or solubilizing agent, besides hydrophilic polymer that itself acts as a surfactant, may be included in the working solution to speed solubilization or dissolution of ingredients such as the active agent therein. Examples of suitable agents include, but are not limited to, Sodium Lauryl Sulfate; Polysorbate 20, 40, 60, 80; Polyoxyethylene glycolated natural or hydrogenated vegetable oils such as polyoxyethylene glycolated natural or hydrogenated castor oils (Cremophor), Poloxamers, Polyoxyethylene 50 Stearate, Propylene Glycol Monostearate, Sorbitan Monolaurate, Sorbitan Monooleate, Sorbitan Monopalmitate, Sorbitan Monostearate, Lanolin Alcohols, Lecithin and others. Such solubilizing agents may be included in the working solution in any suitable amount, for example in an amount of from 0.1 to 10 percent by weight.

6. Pharmaceutical Formulations.

The pellets of the invention can be formulated into various pharmaceutical dosage forms, including capsules and tablets. In one embodiment, the pellets are filled into a hard gelatin capsule, sizes typically ranging from 3, 2, 1, 0, 0 elongated or 00. Tablets can be produced by conventional tabletting techniques with conventional ingredients or excipients. The tablets are preferably formed from a composition comprising the particles described herein distributed in a mixture of a disintegrant and a diluent or filler. Suitable disintegrants include, but are not limited to, crospovidone and croscarmellose. Suitable diluents include, but are not limited to, lactose, sucrose, dextrose, mannitol, sorbitol, starch, cellulose, calcium phosphate, microcrystalline cellulose such as AVICEL™, etc. Tablets may include a variety of other conventional ingredients, such as binders, buffering agents, lubricants, glidants, thickening agents, sweetening agents, flavors, and pigments.

Figure 1:
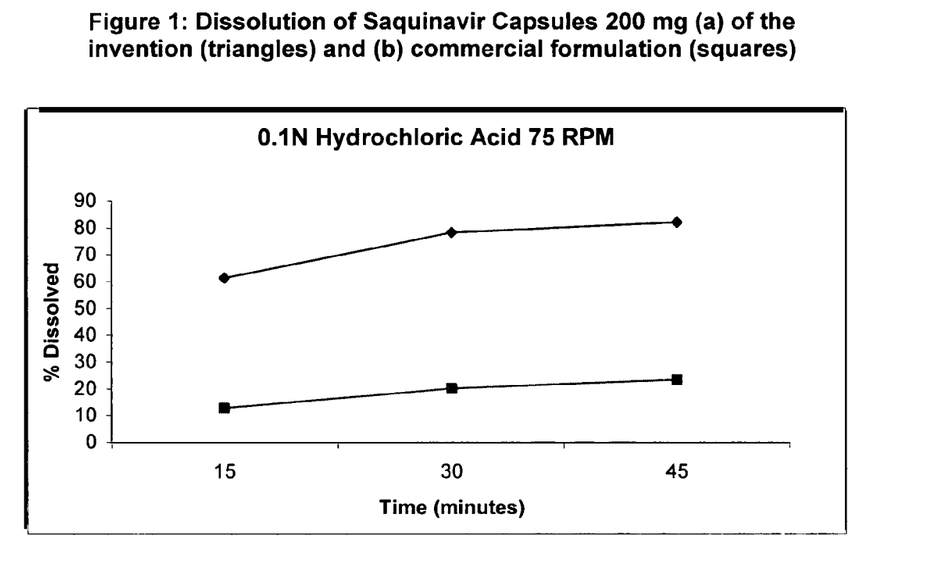
FIG. 1: Dissolution data of Saquinavir capsules of the invention as compared to that of commercially available Saquinavir capsules in 0.1 N Hydrochloric Acid.

In a preferred embodiment of the foregoing, the stabilized formulation of active agent provides increased solubility under pH 5.0 dissolution conditions and thereby results in enhanced bioavailability of the active ingredient under fasted conditions. Table 5 clearly shows that Itraconazole formulation of the invention has approximately 74% higher absorption under fed and 129% higher absorption under fasted conditions as compared to that of Brand formulation under respective conditions. For example, a stabilized formulation of Saquinavir as described herein provides about four fold increased solubility in the first 30 minutes of dissolution under pH 1.2 conditions and thereby may result in enhanced bio-availability of the active ingredient (see FIG. 1). The crystallization of Saquinavir is prevented in the process of the present invention.

Subjects afflicted with a disorder that may be treated with the oral dosage forms described herein include both human subjects and animal subjects (particularly mammalian subjects such as dogs, cats and rabbits). Disorders with which such subjects may be afflicted include those for which the active compounds described above are known to be effective in treating. The dosage of active agent will vary depending upon factors such as the disease and severity thereof, the age, weight and condition of the subject, etc., but in some embodiments is between 0.5 or 50 or 100 milligrams per unit dosage form up to 500 milligrams per unit dosage form. The dosage form or forms may be administered to the subject at a single time or (more preferably) on multiple occasions over the day, and may be administered to the subjects under fed conditions (that is, simultaneously with food, or shortly before or after the subject has eaten so that the residence time of the dosage form in the subject's stomach is longer as compared to fasted conditions) or may be administered to the subject under fasted conditions (that is, without concurrent food administration so that the residence time of the dosage form in the subject's stomach is shorter as compared to fed conditions).

The present invention is explained in greater detail in the following non-limiting examples.

EXAMPLE 1

Saquinavir Preparation

This example describes the preparation of an oral dosage form of Saquinavir in accordance with the methods of the present invention.

A. Ingredients. Ingredients for the preparation of a Saquinavir formulation of the invention are set forth in the table below.

| Unit mg | Ingredient | Formula Weight |
|---|---|---|
| 206.0 | Microcrys. Cell. Spheres([1]) | 61.8 g |
| 200.0 | Saquinavir([2]) | 60.0 g |
| 280.0 | Hydroxypropyl Methyl Cel. 3 CPS grade | 84.0 g |
| 0.0 | Alcohol SD3A Anhydrous Removed([3]) | 777.0 g |
| 0.0 | Purified Water, USP/EP Portion 1 Removed([3]) | 259.0 g |
| 24.0 | Polyethylene Glycol 8000 NF | 7.2 g |
| 0.0 | Purified Water, USP/EP Portion 2 Removed([3]) | 64.8 g |
| 710.0 | Total | 213.0 g (dry solids) |

([1])CP507 grade Celpheres ® are used
([2])Saquinavir vs. HPMC ratio is 1:1.4 by weight. Water and Alcohol ratio is 1:3.
([3])Removed during processing.

Process. SD3A alcohol 777.0 g was taken into a stainless steel container. The hydroxypropyl methyl cellulose (HPMC) was added under stirring. When it formed a uniform suspension, the purified water was added under stirring. The stirring was continued until a translucent solution was formed.

To the above solution, Saquinavir was added and stirring continued until all of active was in solution. When a clear solution was obtained, the pH of the solution was checked. At this stage the weight of the solution was checked and adjusted accordingly with additional quantity of alcohol.

A Strea 1 fluidized bed coater equipped with a Wurster spray insert was used for coating of the particles. The powder generation (spray drying) was avoided and filters were placed properly to avoid losses. The spray rate was gradually increased from a starting rate of 4 g to 7 g per minute towards the end of process. Drug loading was performed at a product bed temperature of 33-43° C. with an air volume of 70-90 CMH (Cubic Meters per Hour) and atomizing air pressure of 2.5 bar. The coated particles are dried for approx. 30 minutes at a target product bed temperature of 45° C. (no more than 48° C.).

The above drug loaded particles were coated with polyethylene glycol dissolved in water using above coating conditions. Polyethylene glycol was dissolved with application of heat (not to exceed 40° C.) until it formed a clear solution. Spraying of solution was done at 5 g per minute and 35° C. (not to exceed 40° C.).

The coated particles were then cured for approximately 30 minutes with a product bed temperature of 45° C. (not to exceed 48° C.). The particles were cooled and unloaded into a polyethylene bag.

The coated particles described above were then used to fill in a size 00, Capsugel™ hard gelatin capsule to provide a finished oral dosage having the ingredient weights and proportions set forth.

EXAMPLE 2

Cyclosporine Preparation

This example describes the preparation of an oral dosage form of Cyclosporine in accordance with the methods of the present invention.

A. Ingredients. Ingredients for the preparation of a Cyclosporine formulation of the invention set forth in the table below.

| Unit mg | Ingredient | Formula Weight |
|---|---|---|
| 225.0 | Microcrys. Cell. Spheres([1]) | 33.75 g |
| 100.0 | Cyclosporine([2]) | 15.0 g |
| 225.0 | Hydroxypropyl Methyl Cel. 3 CPS grade | 33.75 g |
| 0.0 | Alcohol SD3A Anhydrous Removed([3]) | 396.6 g |
| 0.0 | Purified Water, USP/EP Portion 1 Removed([3]) | 132.2 g |
| 100.0 | Cremophor ® RH40 | 15.0 g |
| 650.0 | Total | 97.5 g (dry solids) |

([1])CP507 grade Celpheres ® are used
([2])Cyclosporine vs. HPMC ratio is 1:2.25 by weight. Water and Alcohol ratio is 1:3.
([3])Removed during processing Process. SD3A alcohol 396.6 g was taken into a stainless steel container. The hydroxypropyl methyl cellulose was added under stirring. When it formed a uniform suspension, the purified water was added under stirring. The stirring was continued until a translucent suspension was formed.

To the above solution, Cyclosporine was added and stirring continued until all of active was in solution. To this Cremophor RH 40 was added under stirring. When a clear solution was obtained, the pH of the solution was checked. At this stage the weight of the solution was checked and adjusted accordingly with additional quantity of alcohol.

A mini-Glatt fluidized bed coater equipped with a Wurster spray insert was used for coating of the particles. The powder generation (spray drying) was avoided and filters were placed properly to avoid losses. The spray rate was gradually increased from a starting rate of 1.0 g to a final rate of 2.0 g per minute towards the end of process. Drug loading was performed at a product bed temperature of 33-43° C. with an air volume pressure of 1.0 bar and atomizing air pressure of 2.0 bar. The coated particles were dried for approx. 30 minutes at a target product bed temperature of 45° C. (no more than 48° C.).

The coated particles were then cured for approximately 12-14 hours with a product bed temperature of 50.0° C. (not to exceed 52° C.). The particles were cooled and unloaded into a polyethylene bag.

The coated particles described above were then used to fill in a size 0 elongated, Capsugel™ hard gelatin capsule to provide a finished oral dosage having the ingredient weights and proportions set forth.

EXAMPLE 3

Paclitaxel Preparation

This example describes the preparation of an oral dosage form of Paclitaxel in accordance with the methods of the present invention.

A. Ingredients. Ingredients for the preparation of a Paclitaxel formulation of the invention set forth in the table below.

| Unit mg | Ingredient | Formula Weight |
|---|---|---|
| 422.5 | Microcrys. Cell. Spheres[1] | 42.25 g |
| 30.0 | Paclitaxel[2] | 3.0 g |
| 90.0 | Hydroxypropyl Methyl Cel. 3 CPS grade | 9.0 g |
| 0.0 | Alcohol SD3A Anhydrous Removed[3] | 119.8 g |
| 0.0 | Purified Water, USP/EP Removed[3] | 21.2 g |
| 45.0 | Cremophor ® RH40 | 4.5 g |
| 587.5 | Total | 58.75 g (dry solids) |

[1]CP507 grade Celpheres are used
[2]Paclitaxel vs. HPMC ratio is 1:3.0 by weight.
[3]Removed during processing B. Process. SD3A alcohol 119.8 g was taken into a stainless steel container. To this, Paclitaxel was added and stirring continued until all of active was in solution. The hydroxypropyl methyl cellulose was added under stirring. When it formed a uniform suspension, then purified water was added under stirring. The stirring was continued until it formed a clear solution.

To this Cremophor RH 40 was added under stirring. When a clear solution was obtained, the pH of the solution was checked. At this stage the weight of the solution was checked and adjusted accordingly with additional quantity of alcohol.

A mini-Glatt fluidized bed coater equipped with a Wurster spray insert was used for coating of the particles. The powder generation (spray drying) was avoided and filters were placed properly to avoid losses. The spray rate was gradually increased from a starting rate of 1.0 g to a final rate of 1.5 g per minute towards the end of process. Drug loading was performed at a product bed temperature of 37-43° C. with an air volume pressure of 1.0 bar and atomizing air pressure of 2.0 bar. The coated particles were dried for approx. 30 minutes at a target product bed temperature of 45° C. (no more than 48° C.).

The coated particles were then cured for approximately 12-14 hours with a product bed temperature of 50.0° C. (not to exceed 52° C.). The particles were cooled and unloaded into a polyethylene bag.

The coated particles described above were then used to fill in a size 0, Capsugel™ hard gelatin capsule to provide a finished oral dosage having the ingredient weights and proportions set forth.

EXAMPLE 4

Saquinavir 200 mg Capsule Analytical Methodology

This example describes analytical methodology used to examine the prepared 200 mg saquinavir capsules.
(I) Dissolution.
(A) 0.1 N Hydrochloric Acid (pH 1.2) Simulated Gastric Fluid Procedure. 0.1N Hydrochloric Acid Medium: Add 8.5 mL of 36% Hydrochloric Acid to each Liter of filtered water and mix well.

Standard Preparation: Add approximately 200 mg, accurately weighed, of Saquinavir Free Base material to a Class A 900 mL volumetric flask and dissolve in 9 mL of spectrophotometric grade anhydrous alcohol and dilute to volume with 0.1N Hydrochloric Acid medium.

Sample Preparation: Weigh six individual capsules and record the weights.

Dissolution Conditions: 900 mL of dissolution medium per vessel; USP Apparatus II (Paddles); 100 RPM paddle speed.

Procedure: Proceed as directed in the USP, withdrawing 20 mL of dissolution medium at 15, 30 and 45 minutes after dropping the capsule samples. Determine the absorbance of the standard and samples at 242 nm using a 1 mm flowcell and a suitable UV spectrophotometer.

(B) pH 3 Citrate Buffer Procedure:

pH 3 Citrate Buffer Medium: Add 6.46 mg of anhydrous dibasic sodium phosphate and 18.56 mg of citric acid monohydrate to each Liter of filtered water and adjust the pH to 3.0 using drop wise addition of 85% o-Phosphoric acid, and mix well.

Standard Preparation: Add approximately 200 mg, accurately weighed, of Saquinavir Free Base material to a Class A 900 mL volumetric flask and dissolve in 9 mL of spectrophotometric grade anhydrous alcohol and dilute to volume with pH 3 Citrate Buffer Medium.

Sample Preparation: Weigh six individual capsules and record the weights.

Dissolution Conditions: 900 mL of dissolution medium per vessel; USP Apparatus II (Paddles); 100 RPM paddle speed.

Procedure: Proceed as directed in the USP, withdrawing 20 mL of dissolution medium at 15, 30 and 45 minutes after dropping the capsule samples. Determine the absorbance of the standard and samples at 239 nm using a 1 mm flowcell and a suitable UV spectrophotometer.

(C) pH 5 Phosphate Buffer Procedure:

20 mM pH 5 Phosphate Buffer Medium: Add 2.83 g of anhydrous dibasic sodium phosphate to each Liter of filtered water and adjust the pH to 5.0 using drop wise addition of 85% o-Phosphoric acid, and mix well.

Standard Preparation: Add approximately 200 mg, accurately weighed, of Saquinavir Free Base material to a Class A 900 mL volumetric flask and dissolve in 9 mL of spectrophotometric grade anhydrous alcohol and dilute to volume with pH 5 Phosphate Buffer Medium.

Sample Preparation: Weigh six individual capsules and record the weights.

Dissolution Conditions: 900 mL of dissolution medium per vessel; USP Apparatus II (Paddles); 100 RPM paddle speed.

Procedure: Proceed as directed in the USP, withdrawing 20 mL of dissolution medium at 15, 30 and 45 minutes after dropping the capsule samples. Determine the absorbance of the standard and samples at 239 nm using a 1 mm flowcell and a suitable UV spectrophotometer.

(II) UV Assay:

To perform a quick in-process assay of drug loaded beads an assay procedure by UV spectrophotometric method was developed and described below.

Transfer an accurately weighed quantity of beads equivalent to 200 mg of Saquinavir into a dry 900 mL Class A volumetric flask which contains approximately 400 mL of 0.1N Hydrochloric Acid Medium, and sonicate for 10 minutes to disassociate the Saquinavir material from the Celphere beads. Dilute the flask contents to volume with 0.1N Hydrochloric Acid Medium and mix well. Determine the absorbance of the sample at 242 nm using a 1 mm flowcell and a suitable UV spectrophotometer. Use standard reading for calculation of Saquinavir content.

(III) HPLC Assay:

The procedure is used for determination of Saquinavir and related impurity contents in the capsules.

The HPLC method used in the analysis originated as a USP assay method for the determination of Saquinavir Mesylate. It has been adapted and modified during its use at DSM. The procedure is as below:

Mobile Phase: pH 2.5 Triethylamine Buffer:Tetrahydrofuran:Acetonitrile (60:33:7)

pH 2.5 Triethylamine (TEA) Buffer: Add 18 mL of TEA to a suitable container containing 1800 mL of filtered water and pH adjust to 2.5 using 85% o-phosphoric acid. (Note: Filtered water refers to water that has been steam distilled and further purified by ultra filtration.)

Add the entire buffer solution to a 4 Liter bottle containing 990 mL of Tetrahydrofuran (THF) and 210 mL of Acetonitrile (ACN) and mix well. Note: All reagents are HPLC grade or better.

| Analysis Type | Reversed Phase Isocratic HPLC |
|---|---|
| Column | Spherisorb 5 ODS 2 4.6 × 250 mm |
| Injection Volume | 20 µl |
| Flow Rate | 0.8 mL per minute |
| Column Temp. | 20° C. |
| Wavelength | 210 nm |
| Run Time | 40 minutes |

Standard Preparation: Add approximately 200 mg of Saquinavir standard, accurately weighed, to a 100 mL volumetric flask and dissolve in 30 mL of anhydrous alcohol, dilute to volume with mobile phase and mix well. Pipet 5 mL of this solution into a 50 mL volumetric flask and dilute to volume with mobile phase and mix well.

Sample Preparation: Sample Diluent: Add 600 mL of anhydrous alcohol and 400 mL of filtered water to a suitable container and mix well.

Bead based formulation and Soft Gel formulation (i.e. Fortovase saquinavir formulation) (Note: Fortovase is a soft gelatin saquinavir capsule containing a thick liquid): Empty and combine the contents of not fewer than 10 capsules. Transfer an amount of Capsule contents, equivalent to 200 mg of Saquinavir, to a 100 mL volumetric flask, and add 70 mL of Diluent. Sonicate the flask for approximately 10 minutes, dilute to volume with Diluent, and mix well. Pipet 5 mL of this solution into a 50 mL volumetric flask, dilute to volume with Diluent and mix well.

Procedure: Using a suitable HPLC with the conditions described above, chromatograph a Diluent injection, followed by 6 Standard injections. Then using bracketing standards, chromatograph a single injection of the standard check followed by duplicate injections of each sample. The % l. s. of the standard check must fall between 98 to 102%, and the % RSD of the retention times and peak areas of Saquinavir for the 6 standards must be less than 2%.

Saquinavir dissolution results are given in Tables 1-3 below:

TABLE 1

Dissolution Comparison - Invention vs Commercial Capsules
Conditions: USP Type 2 (paddle, RPM 75)
Medium Used: 0.1 Hydrochloric Acid

| Time Interval | Invention | Commercial |
|---|---|---|
| 15 | 61.4 | 12.8 |
| 30 | 78.2 | 20.2 |
| 45 | 82 | 23.5 |
| Min at 45 mins. | 78 | 22.1 |
| Max at 45 mins. | 85.4 | 25.3 |

TABLE 2

Dissolution Comparison - Invention vs Commercial Capsules
Conditions: USP Type 2 (paddle, RPM 100)
Medium Used: pH 5 Phosphate Buffer

| Time Interval | Invention | Commercial |
|---|---|---|
| 15 | 98.3 | 90.6 |
| 30 | 100.1 | 102.7 |
| 45 | 100.4 | 102.3 |
| Min at 45 mins. | 100.1 | 102.1 |
| Max at 45 mins. | 100.8 | 102.7 |

TABLE 3

Dissolution Comparison - Invention vs Commercial Capsules
(Conditions: USP Type 2 (paddle, RPM 100);
Medium Used: Ph 3.0 Citrate Buffer)

| Time Interval | Invention | Commercial |
|---|---|---|
| 15 | 82.2 | 91.1 |
| 30 | 98.7 | 99.6 |
| 45 | 99.4 | 99.8 |
| min. at 45 mins. | 97.6 | 99.1 |
| max. at 45 mins. | 100.6 | 100.6 |

The above dissolution data clearly indicate approximately four fold enhanced solubility of products of the instant invention in 0.1N hydrochloric acid medium as that of the commercial formulation, although there is comparable dissolution results under pH 3.0 and 5.0 buffer conditions. For immediate release dosage forms, pH 1.2 dissolution conditions are preferred.

EXAMPLE 5

Stability of Saquinavir in the Formulation of the Invention Compared to Soft Gel Saguinavir Commercial Formulation Each hard gelatin capsule of the present invention contains 200 mg of Saquinavir (bead based technology). Each soft gelatin capsule of commercially available FORTOVASE Saquinavir formulation contains 200 mg of Saquinavir (lipid based system). Samples are stored at 50° C. for six weeks. Stability data is given in the Table 4 below.

TABLE 4

Invention vs. Commercial Formulations stability

| Formulation | Initial* | 6 weeks* | Percent decrease |
|---|---|---|---|
| Hard Gelatin Capsule - Invention | 99.55 | 98.43 | 1.12 |
| Soft Gelatin Capsule - Commercial | 98.39 | 90.26 | 8.13 |

*Values are in percent area of Saquinavir peak

These data indicate that the bead based formulation of the present invention has relatively good stability under above temperature condition storage. Note that FORTOVASE Saquinavir formulation requires storage at 2-8° C.

EXAMPLE 6

Amorphous Form of Active Ingredient

In order to confirm that the active is in amorphous form, Differential Scanning Calorimetry (DSC) was carried out on active pharmaceutical ingredients and the drug loaded particles prepared during the spray coating process. Also Itraconazole formulations of the invention and commercial formulations were dosed in to Humans to perform bioavailability studies. Results are shown below.

Figure 2:
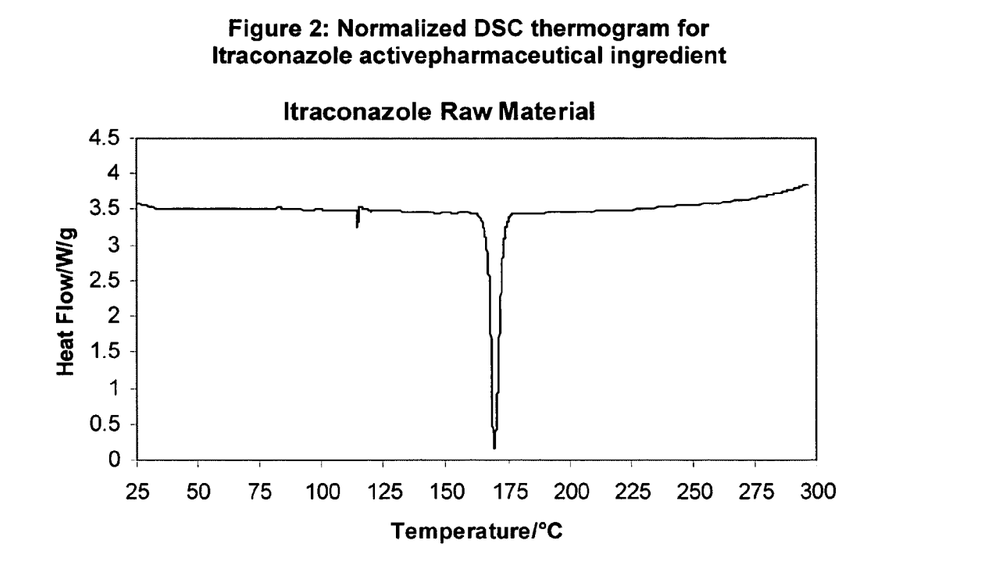
FIG. 2: Normalized DSC thermogram for Itraconazole active pharmaceutical ingredient.

1. Itraconazole Active pharmaceutical ingredient. The resulting DSC thermogram from Itraconazole active pharmaceutical ingredient is shown in FIG. 2. Itraconazole exhibits a sharp melt at approximately 170° C., with a melting enthalpy of 85.1 J/g. The sharp nature of the melt indicates that the Itraconazole crystals are relatively free from defects and of uniform size.

Figure 3:
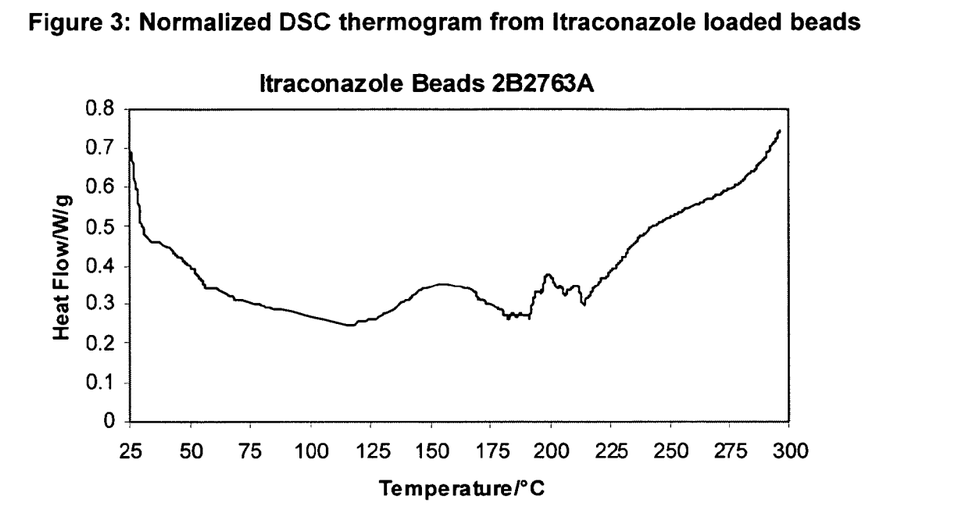
FIG. 3: Normalized DSC thermogram from Itraconazole-loaded beads.

2. Itraconazole-loaded Beads according to the present invention. The thermogram from Itraconazole loaded beads is shown in FIG. 3. The signature melting of Itraconazole at 170° C., seen in FIG. 2, is not evident in these samples. The absence of the Itraconazole melting endotherm indicates that the Itraconazole has adopted an amorphous form in the formulation.

Figure 4:
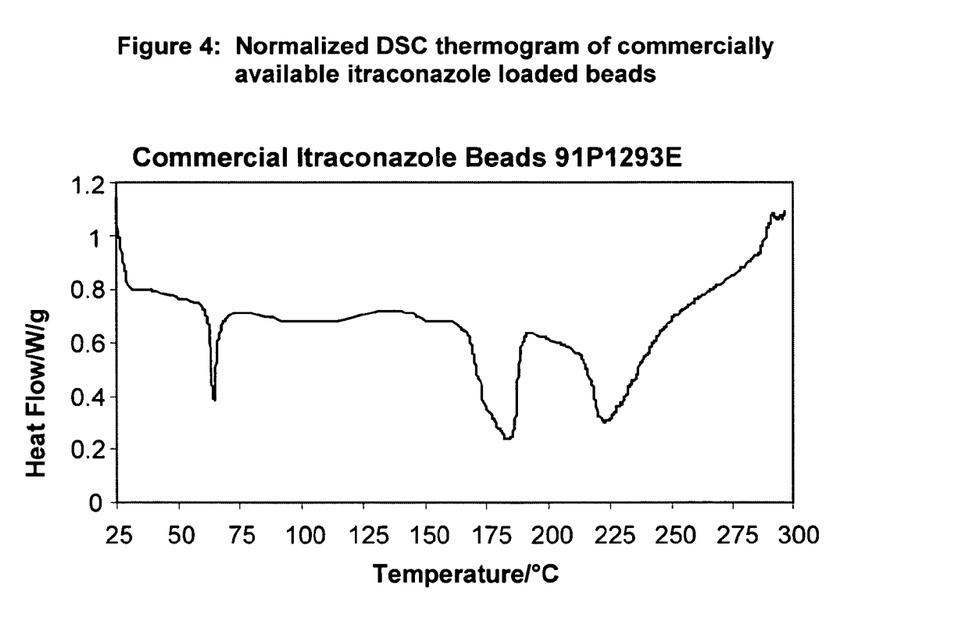
FIG. 4: Normalized DSC thermogram from a commercially available itraconazole bead.

3. Commercial Formulation of Itraconazole. A DSC thermogram from a commercial formulation of Itraconazole available as SPORANOX is shown in FIG. 4. This scan is highly reproducible and shows three distinct melting phenomena:PEG melts at approximately 60° C., sucrose melts between 165° C. and 185° C. and Itraconazole melts at 225° C.

Figure 11:
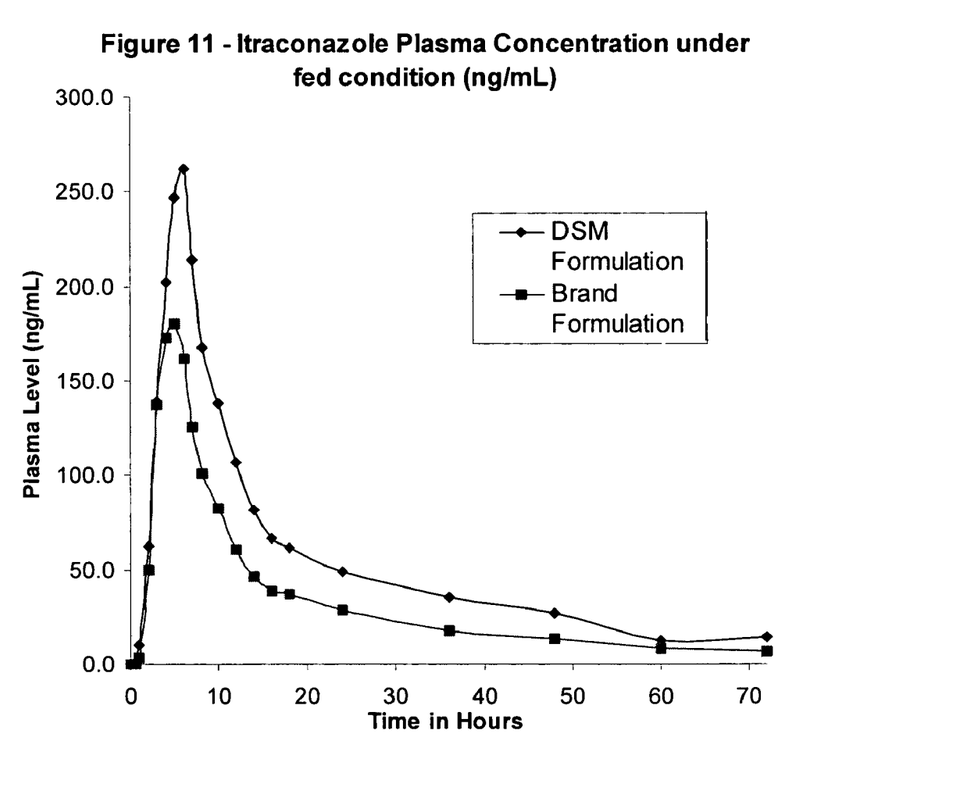
FIG. 11: Itraconazole plasma concentration in Humans under fed condition.
Figure 12:
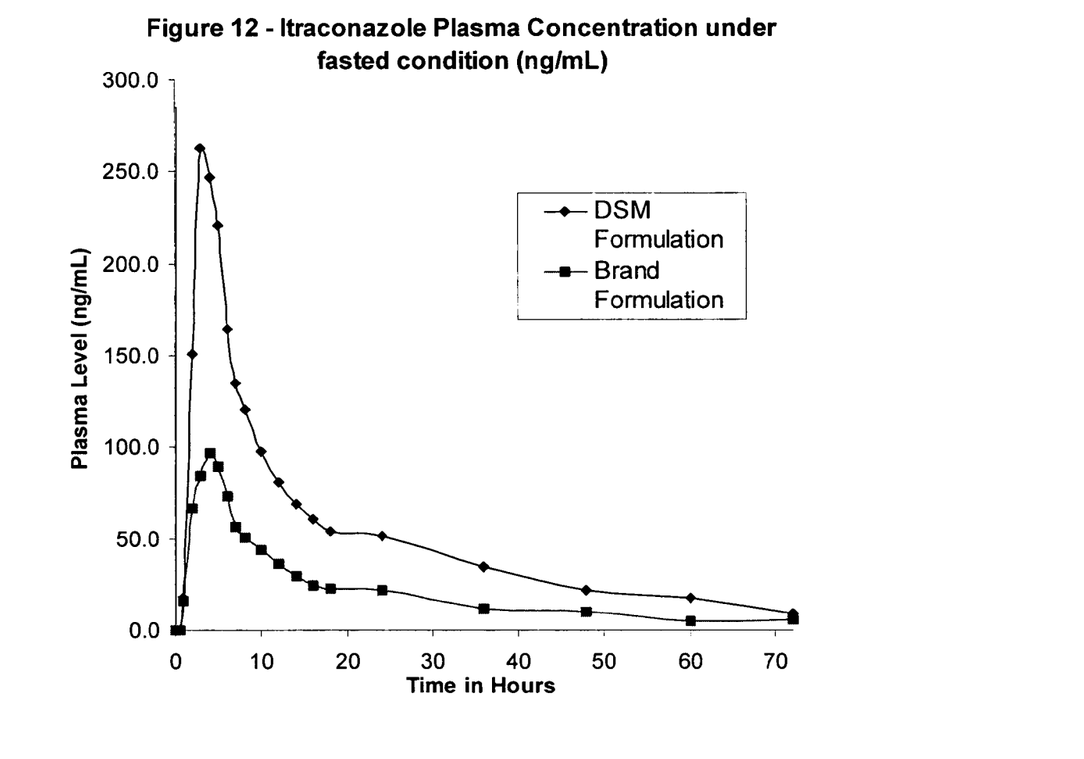
FIG. 12: Itraconazole plasma concentration in Humans under fasted condition.

Commercial formulation shows some amount of crystalline material and has different dissolution profiles under pH 5.0 conditions. Enhanced dissolution of invention formulation under pH 5.0 conditions has resulted in better bio-availability of Itraconazole as shown in Table 5. FIGS. 11 and 12 show enhanced absorption of Itraconazole with formulations of the invention when orally administered.

TABLE 5

Bio-study Results of Itraconazole Formulations

|  | AVC 0-Inf. (ng · h/mL) | Cmax (ng/mL) | Tmax (h) |
|---|---|---|---|
|  | Fasted Conditions | | |
| DSM Drug Product | 3635 (129% higher) | 279.1 | 3.7 |
| Commercial Drug Product | 1588 | 113.9 | 3.84 |
|  | Fed Conditions | | |
| DSM Drug Product | 4537 (74% higher) | 271.5 | 5.51 |
| Commercial Drug Product | 2609 | 193.9 | 4.67 |

Figure 5:
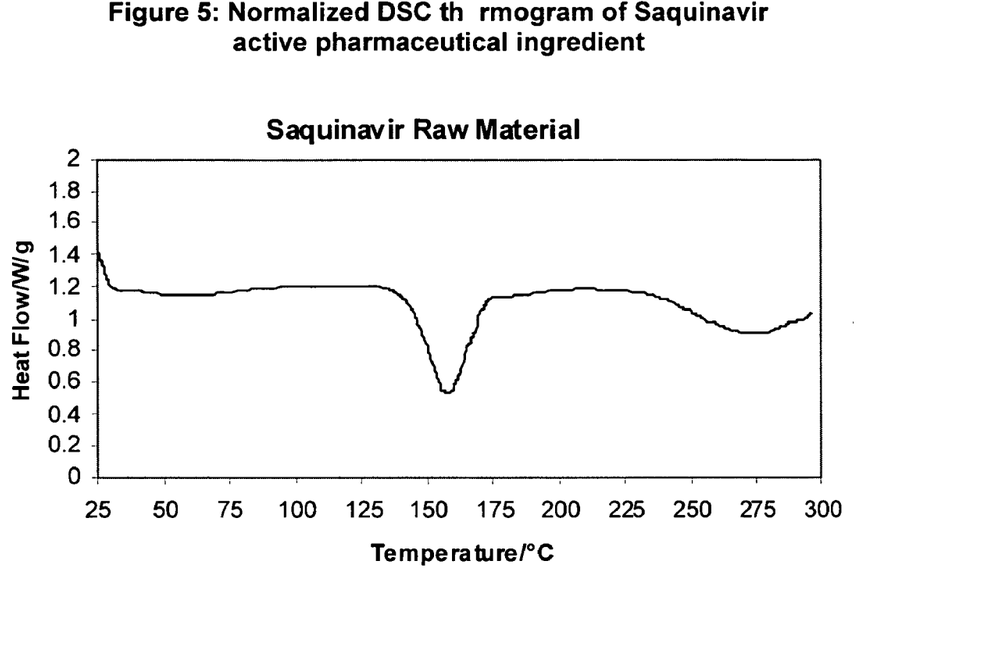
FIG. 5: Normalized DSC thermogram from Saquinavir active pharmaceutical ingredient.

4. Saquinavir Active Pharmaceutical Ingredient. A normalized DSC thermogram from Saquinavir is shown in FIG. 5. The sample of Saquinavir exhibits a distinct melting endotherm that peaks at 158° C. The melting enthalpy of Saquinavir is 68±2 J/g. The melt is quite broad, indicating relatively small and imperfect crystals.

Figure 6:
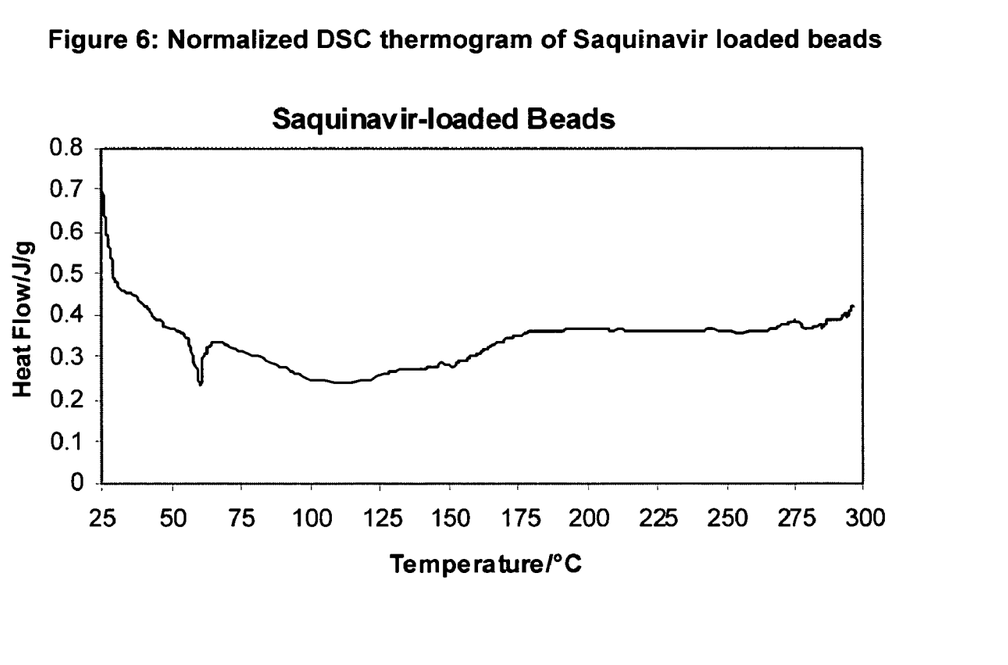
FIG. 6: Normalized DSC thermogram from Saquinavir-loaded beads.

5. Saquinavir Loaded Beads according to the present invention. The normalized DSC thermogram from Saquinavir loaded beads is shown in FIG. 6. The thermogram from Saquinavir loaded beads is absent of any Saquinavir melting endotherm, indicating that this material is present in amorphous form. There is a small endotherm peak at 58° C. due to polyethylene glycol.

Figure 7:
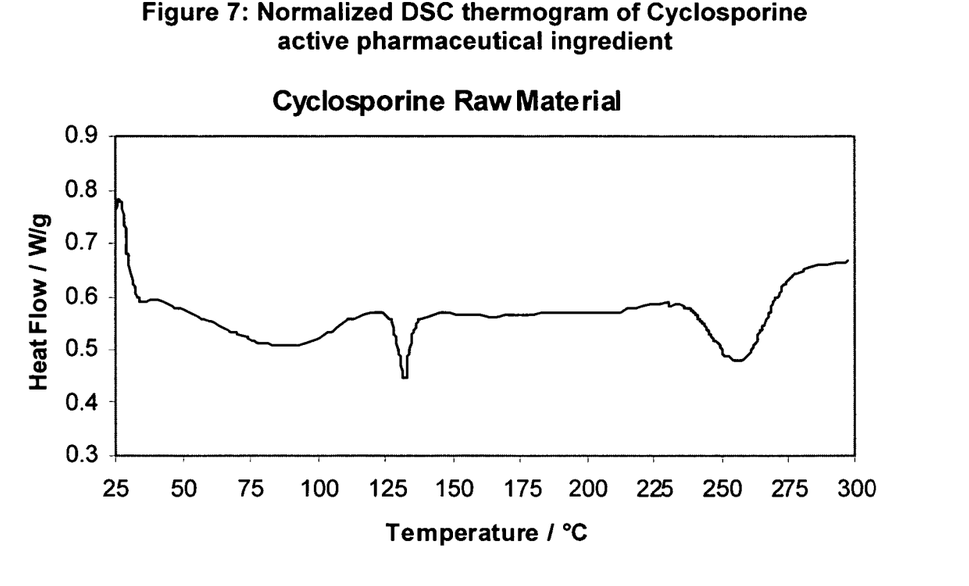
FIG. 7: Normalized DSC thermogram of Cyclosporine active pharmaceutical ingredient.
Figure 8:
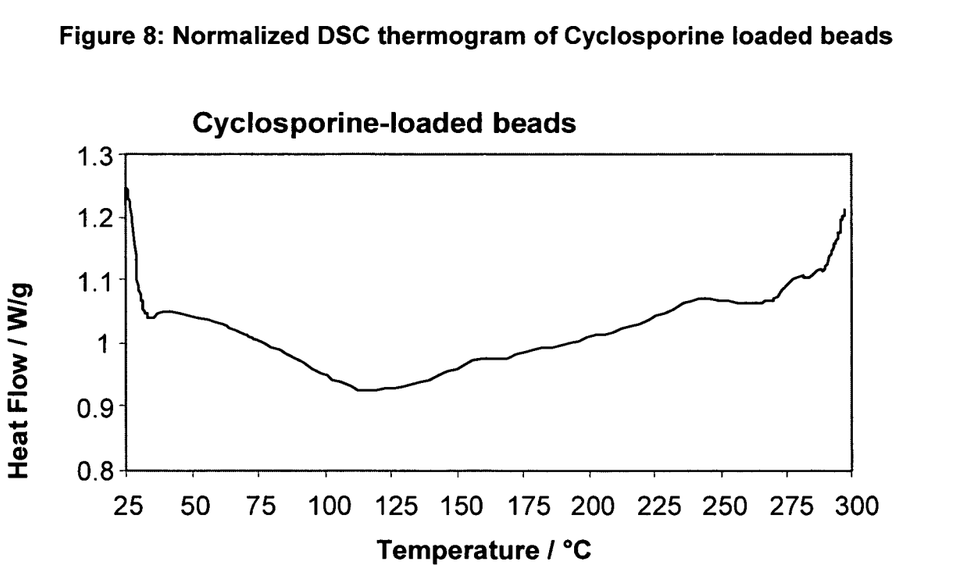
FIG. 8: Normalized DSC thermogram of Cyclosporine loaded beads.

6. Cyclosporine Active Pharmaceutical Ingredient and the Active Loaded Beads according to the present invention. The thermograms are shown in FIGS. 7 and 8, respectively. The resulting DSC thermogram from Cyclosporine active pharmaceutical ingredient exhibits a melt at approximately 130° C. with melting enthalpy of 4.52±0.04 J/g. There is a second endothermic event at around 260° C. that is likely due to degradation of Cyclosporine. If it is related to degradation it should be unaffected by the morphological state of the material. Quantitative analysis shows this to be the case. The signature melting of Cyclosporine at 130° C. is not evident in the sample. The absence of the Cyclosporine melting endotherm indicates that the drug has adopted an amorphous form of some kind in the formulation.

Figure 9:
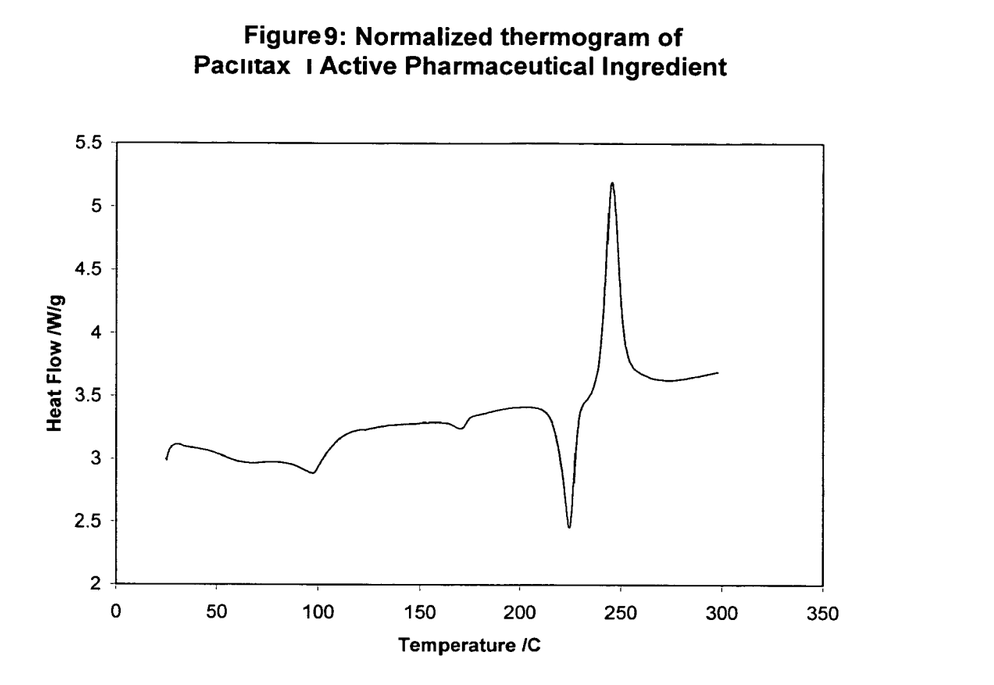
FIG. 9: Normalized DSC thermogram of Paclitaxel active pharmaceutical ingredient.
Figure 10:
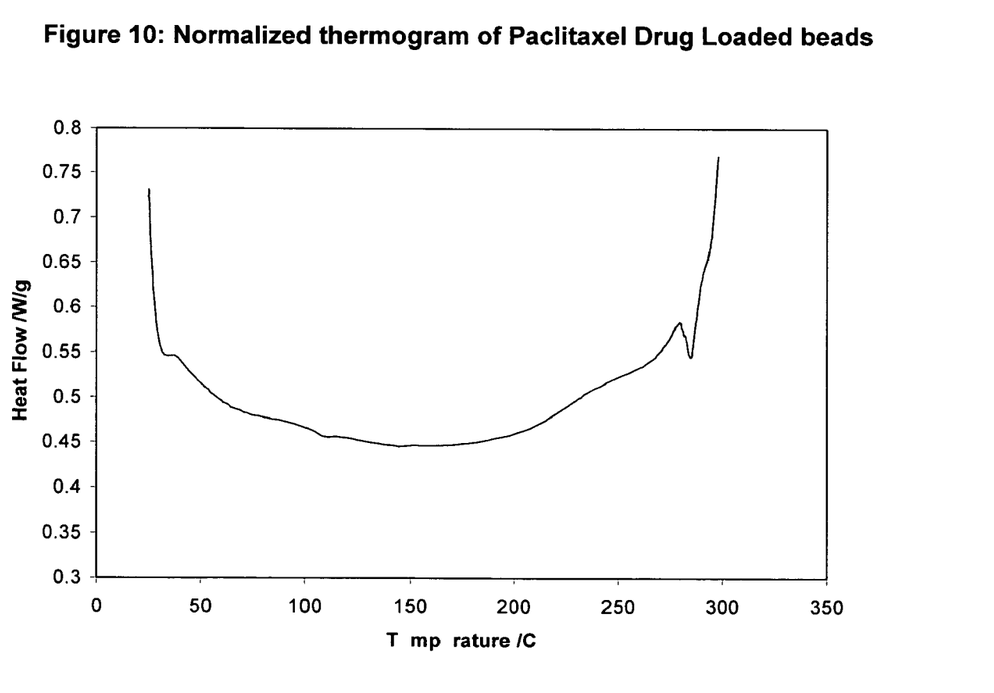
FIG. 10: Normalized DSC thermogram of Paclitaxel loaded beads.

7. Paclitaxel Active Pharmaceutical Ingredient and the Active Loaded Beads according to the present invention. Thermograms are shown in FIGS. 9 and 10, respectively. There were two melts at 98.2° C. and 171.06° C. in the thermogram of Active Pharmaceutical Ingredient with enthalpy values 16.79 J/g and 3.96 J/g respectively. The transformations that are seen in thermogram of Paclitaxel above 200° C. are absent in that of the drug loaded beads indicating that Paclitaxel is present in a different form in beads and there-by the beads containing Paclitaxel show enhanced solubility under dissolution conditions.

The foregoing is illustrative of the present invention, and is not to be construed as limiting thereof. The invention is defined by the following claims, with equivalents of the claims to be included therein That which is claimed is:

1. A method of manufacturing a water-insoluble azole antifungal active agent-oral dosage form, said method comprising the steps of:

providing a single phase working solution comprising a water-insoluble azole antifungal active agent, water, a water-soluble polymer and a solvent, said solvent selected from the group consisting of alcohol, acetone, and mixtures thereof;

providing core particles formed from a pharmaceutically acceptable material;

combining said working solution with said particles to produce water-insoluble azole antifungal active agent-coated particles;

drying said water-insoluble azole antifungal active agent-coated particles; and forming said dried particles into an oral dosage form;

wherein said working solution is essentially free of methylene chloride, and said oral dosage form is essentially free of methylene chloride.

2. The method of claim 1, further comprising the step of adjusting the pH of said working solution to solubilize said water-insoluble azole antifungal active agent prior to said providing step.

3. The method of claim 1, wherein said working solution further comprises a surfactant.

4. The method according to claim 1, wherein said single phase working solution has a viscosity of from 10-2000 mPa.s during said combining step.

5. The method according to claim 1, wherein the ratio of water-insoluble azole antifungal active agent-to water-soluble polymer in said working solution is from 1:0.5 to 1:20 on a weight: weight basis.

6. The method according to claim 1, wherein the ratio of solvent to water in said working solution is from 50:50 to 95:5 on a weight: weight basis.

7. The method according to claim 1, wherein said water-insoluble azole antifungal active agent comprises active agent in amorphous form.

8. The method according to claim 1, wherein said alcohol is selected from the group consisting of methanol, ethanol, propanol, butanol, and mixtures thereof.

9. The method according to claim 1, wherein said water-soluble polymer is selected from the group consisting of hydroxypropyl methylcellulose, methacrylate, hydroxypropylcellulose, polyvinylpyrrolidones, dextrins and maltodextrins.

10. The method according to claim 3, wherein said surfactant is selected from the group consisting of Sodium Lauryl Sulfate, Polysorbate 20, 40, 60, or 80, Polyoxyethylene glycolated natural or hydrogenated vegetable oils, hydrogenated castor oils, Poloxamer, Polyoxyethylen 50 Stearate, Propylene Glycol Monostearate, Sorbitan Monolaurate, Sorbitan Monooleate, Sorbitan Monopalmitate, and Sorbitan Monostearate.

11. The method according to claim 1, wherein said core particles comprise microcrystalline cellulose spheres.

12. The method according to claim 1, wherein said core particles comprise mannitol spheres.

13. The method according to claim 1, wherein said core particles are from 100 to 1000 micrometers in diameter.

14. The method of claim 1, wherein said drying step is followed by the step of coating said spheres with an external coating.

15. The method according to claim 1, wherein the water-insoluble azole antifungal active agent is ketoconazole.

* * * * *